United States Patent [19]

Zimmermann et al.

[11] 4,289,756

[45] * Sep. 15, 1981

[54] PHYSIOLOGICAL PREPARATION CONTAINING LOADED CELLS OF EXPANDED VOLUME IN SUSPENSION, FOR PREFERENTIAL ACCUMULATION IN SPLEEN AND LIVER

[75] Inventors: Ulrich Zimmermann, Jülich; Günter Pilwat, Niederzier; Karin Bock, Aachen; Hermann J. Buers, Jülich, all of Fed. Rep. of Germany

[73] Assignee: Kernforschungsanlage Jülich GmbH, Jülich, Fed. Rep. of Germany

[ * ] Notice: The portion of the term of this patent subsequent to Sep. 23, 1997, has been disclaimed.

[21] Appl. No.: 860,570

[22] Filed: Dec. 14, 1977

[30] Foreign Application Priority Data

Dec. 15, 1976 [DE] Fed. Rep. of Germany ....... 2656746

[51] Int. Cl.$^3$ ..................... A61K 37/48; A61K 43/00; A61K 35/14
[52] U.S. Cl. ........................ 424/101; 424/1; 424/94; 424/106; 435/2
[58] Field of Search ............................ 424/101; 435/2; 195/1.8

[56] References Cited

U.S. PATENT DOCUMENTS 3,887,698  6/1975  McConnell et al. .................. 424/88

FOREIGN PATENT DOCUMENTS 2326224  5/1974  Fed. Rep. of Germany .
2326161  12/1974  Fed. Rep. of Germany .
2326191  12/1974  Fed. Rep. of Germany .
2405119  9/1975  Fed. Rep. of Germany .

OTHER PUBLICATIONS

U. Zimmermann et al., Biochim. et Biophys. Acta, 436, Jun. 17, 1976, 460–474, Enzyme Loading of Electrically Homogeneous Human Red Blood Cell Ghosts Prepared by Dielectric Breakdown.
T. Steck, Chem. Abst. 77: 30542k (1977), Cross-linking the Major Proteins of the Isolated Erythrocyte Membrane.
U. Zimmermann et al., Z. Naturforsch 29, pp. 304–305 (1974).
C. Colley et al., Chemical Abstracts 83: 22192e, Liposomes as Carriers in Vivo for Methotrexate (1975).
H. Kimelberg, Chemical Abstracts 85: 186467r, Differential Distribution of Liposome-entrapped H$^3$-methotrexate and Labeled Lipids after Intravenous Injection in a Primate (1976).
H. Kimelberg et al., Chemical Abstracts 85: 116483u, The Effect of Entrapment in Liposomes on the in Vivo Distribution of H$^3$—methotrexate in a Primate (1976).
U. Zimmermann et al., Chemical Abstracts 82: 108324r, Preparation of Erythrocyte Ghosts by Dielectric Breakdown of the Cell Membrane (1975).
U. Zimmermann et al., Chemical Abstracts 81: 75566v, Reversible Dielectric Breakdown of Cell Membranes in Electrostatic Fields (1974).
U. Zimmermann et al., Chemical Abstracts 85: 29784z, Enzyme Loading of Electrically Homogeneous Human Red Blood Cell Ghosts Prepared by Dielectric Breakdown (1976).

Primary Examiner—Donald G. Daus
Assistant Examiner—M. C. Eakin
Attorney, Agent, or Firm—Frishauf, Holtz, Goodman & Woodward

[57] ABSTRACT

Loaded cells suspended in a physiological solution are prepared in a process in which their volume is expanded by osmotic pressure. Cells so prepared suspended in a physiological solution, when injected into the bloodstream of a living body are preferentially accumulated in the spleen and liver of the body, which treats them as foreign bodies, even though the original cells may have been cells of an animal of the same species. Similarly by storing the loaded cells in a solution containing substances such as glutadialdehyde, formaldehyde that react with the protein phase of membranes or which, like difluoro dinitrobenzene, react with the lipid layer thereof, the loaded cells can also be caused to be broken down by the spleen and/or liver. Premature release of the contents of the loaded cells is prevented and timely release of such contents is assured by incorporating other materials into the loaded cells during the preparation process in accordance with the related application of the same inventors, Ser. No. 859,240 filed Dec. 9, 1977, now U.S. Pat. No. 4,224,313, issued Sept. 23, 1980.

2 Claims, No Drawings

PHYSIOLOGICAL PREPARATION CONTAINING LOADED CELLS OF EXPANDED VOLUME IN SUSPENSION, FOR PREFERENTIAL ACCUMULATION IN SPLEEN AND LIVER

This invention relates to a process of preparation of a physiological solution containing a mass of loaded cells in suspension, such cells having a concentration of material loaded therein designed for chemical or physical interaction with substances located outside of the cell membrane. In such a process, the permeability of living animal cells of the kind having a cell membrane suspended in a cell-compatible solution is increased by the effect of osmotic pressure or by the effect of an electric field. In such a process, also, the interaction material or materials are drawn out of the surrounding cell-compatible solution by permeation through the cell membranes of which the permeability has been increased with simultaneous exchange with the cell content in the interior of the cells to be loaded, and then the material or materials in question are locked in the cells by regeneration of the cells that heals the changes produced in the cell membrane by the effect of osmotic pressure or by the effect of an electric field, after which the loaded cells are separated from the cell-compatible solution containing the loading material and are suspended for preservation and storage in a physiological solution having an osmolarity that corresponds to the osmolarity of the content of the loaded cells. The term "osmolarity" refers to a concentration of particles of molecular size in terms of the osmotic pressure, so that the preceding statement refers to a solution in which osmosis will not occur during storage.

Processes of the above kind for preparation of a suspension of loaded cells in a physiological solution are known from German Pat. No. 23 26 224 and from German published patent applications (OS) 23 26 161 and No. 24 05 119. The patent just mentioned relates to processes for incorporating of complex-forming materials in loaded cells obtained from living cells of living organisms. The processes disclosed in German (OS) No. 23 26 161 concern the incorporation of catalytically active materials such as enzymes or pharmaceutics in loaded cells. Both of the processes just mentioned seek to increase the permeability of the cell membrane by the action of osmotic pressure on the membrane. In the process disclosed in German (OS) No. 24 05 119, on the other hand, the increase of the permeability is obtained by the effect of an electric field.

In addition to the designation "loaded cells" which is intended to express that the cells are "loaded" with materials that are distinct from the normal cell content, other terms have been used for the products of the known processes of the above-described kind, such as "membrane vesicles", "ghost cells" and "membrane envelopes".

As cells for the known processes for preparing a mass of suspended loaded cells, there are used both cells that occur as individual cells in a physiological solution, as for example erythrocytes, lymphocytes, thrombocytes or leukocytes and also cells, such as for example liver cells that are organized in tissues as associations of cells clinging one to another. The cell binding of a tissue is releasable by biochemical or biophysical procedures, so that in this fashion also a suspension of cells in a solution can be obtained.

In the performance of the known processes, particularly for incorporation of extraneous materials in the loaded cells, a specific property of the membrane of living cells is used, namely that a permeability increase produced within certain limits can be reduced back to normal by healing through regeneration of the cells. The healed membrane of the loaded cells thus regains the semipermeable properties of the membrane of the original cells. Apart from the cases in which materials are used which destroy the membrane after their incorporation in the loaded cells and are thereby set free, it is then possible to bring the material incorporated in the loaded cells into interaction with substances present in a physiological solution outside of the loaded cells without the material incorporated and locked in the loaded cells getting into the physiological solution. This takes place when the loaded cells are immersed into the physiological solution containing the substances in question and the substance, by permeation, seeps through the semipermeable membranes of the loaded cells. It is thus possible, for example, with the enzyme invertase locked in loaded cells, to convert cane sugar (sucrose) into glucose and fructose, since cane sugar as well as glucose and fructose get through the membrane, while the enzyme invertase remains locked in the loaded cells. It is also possible, for example, to load cells with urease and then to inject the loaded cells thus produced into the blood vessels of a human body without releasing the urease out of the loaded cells into the blood, and thereby to break down urea contained in the blood which penetrates into the loaded cells.

There is a disadvantage, however, in the loaded cells produced according to known methods, in that the reaction of the materials locked into the loaded cells with the substances present outside the cell membrane are spread out over the entire region occupied by the physiological solution in which the loaded cells are suspended and consequently the effect of the material in the loaded cells cannot be concentrated at a preferred location in the physiological solution. If, for example, loaded cells formed of erythrocytes are injected in the blood circulation system of an animal body, then in the case of a mass of loaded cells produced according to a known method, the effect of the material locked in the loaded cells is spread out over the entire body of the animal. A limitation or concentration of the effect, for example of a medicament locked into the loaded cells, to a particular location within the blood circulation system of the body, or even to a particular organ of the body, is not possible with the loaded cells formed according to the known process.

THE PRESENT INVENTION

It is an object of the present invention to provide a process for producing a suspension of loaded cells in a physiological solution that makes it possible to concentrate the effectiveness of materials locked in the loaded cells injected into the blood circulation system of an animal body in the spleen and/or the liver of the body by controlled release from the loaded cells.

Briefly, in the loading of the cells, there is incorporated into the loaded cells, together with at least one medicament or radionuclide material provided for interaction with substances present in the spleen and/or the liver of an animal body, additional substances of organic or inorganic constitution that are compatible with the membranes of the cells and have a reflection coefficient with respect to the regenerated membranes of the cells that is as close as possible to 1, such additional materials being provided in the cell-compatible solution for loading the cells in such dosing that after incorporation of the aforesaid materials and substances into the loaded cells, the size and/or the shape of the loaded cells are sufficiently differentiated from the size and/or the shape of the same cells before the loading operation, that the loaded cells after their injection into the blood circulation system of an animal body are separated out of the blood by the function of the spleen and liver and broken down by them.

The substances having a reflection coefficient of 1 with reference to the regenerated membranes of the cells are reflected 100% at the membrane and thus remain entirely in the loaded cells after their original incorporation therein. In consequence, water is sucked into the loaded cells, causing the loaded cells to expand until they reach a thermodynamic equilibrium. The increase in volume depends upon the particle concentration of the osmotically active substances in the loaded cells.

The object of the invention is also reached by a process of producing loaded cells that is distinguished by the fact that first at least one medicament material or radionuclide is locked into the loaded cells that is intended to interact with substances present in the spleen and/or the liver of an animal body, and then the loaded cells are put into an isotonic solution containing organic substances which are capable, by reaction with the lipid or protein layer of the membrane, of changing the membrane, as set forth just below, without destruction of the loaded cells, the loaded cells being allowed to stand in the isotonic solution for such a time and the concentration of the substances capable of reacting with the lipid or protein layer being so selected, that the loaded cells, after their injection into the blood stream of an animal body, will be separated out of the blood and broken down by the function of the spleen and liver organs of the body. Substances that react with the lipid or protein layer of the membranes are substances with reactive groups, such as for example glutadialdehyde or formaldehyde, that react with the protein phase, as well as difluordinitrobenzene, that reacts with the lipid phase or also lectins. The use of these substances for the performance of the process according to the invention has, in addition, the advantage that the membranes of the loaded cells are stabilized thereby.

By the volume change—possibly connected with a conversion of the loaded cells—as well as by the change of the membranes of the loaded cells, it is thought that the loaded cells are treated by the spleen as if they were foreign bodies, are therefore taken out of the blood and operated on. The materials locked into the loaded cells are accordingly set free and are transported by preference to the liver through the portal vein system. It is thus possible in a simple way by the use of loaded cells produced in accordance with the present invention, to release medicaments or even other materials, as for example radionuclides in the interior of the spleen or of the liver.

An advantageous further development of the invention concerns the case which at least one material incorporated into the loaded cells along with the osmotically active substances of the kind just described for the purposes of the invention, which first mentioned material if incorporated in the loaded cells without also incorporating still other materials, would have a destructive effect upon the cell membranes that would lead to a premature and uncontrolled release of the material into the physiological solution. In accordance with the further development of the invention there is in such cases incorporated into the loaded cells, at the same time as the first mentioned material, additional materials capable of interacting with the first mentioned material with the formation of hydrogen-bridge-bonds or covalent bonds thereby preventing the first mentioned material from reacting with the cell membranes, without, however, impairing the capability of the first mentioned material for interacting with substances in the physiological solution outside the loaded cells. The preparation of suspensions of loaded cells containing such additional material and suspended in a physiological solution is the subject of our copending U.S. patent application Ser. No. 859,240 filed Dec. 9, 1977, now U.S. Pat. No. 4,224,313, where examples of such preparation are described in detail. In general, such additional material is most readily provided in the form of a protein, such as albumin, or a sugar such as for example, sucrose, and the additional material is incorporated in the loaded cells from the physiological solution to which the cells are exposed when their permeability has been increased, in such dosing as to inhibit the interaction of material in the loaded cells with the cell membranes for a predetermined period of time after the locking in of the various materials loaded into the cells by the restoration of the original semi-permeability of the cells. By the incorporation of an additional material as just described, it is possible to utilize the present invention for transporting by loaded cells through blood vessels for delivery to the spleen or to the liver of a living body even such materials which if they were incorporated alone into the loaded cells would cause a premature destruction of the cell membrane and would therefore fail to be delivered to their destination in those organs of the body.

A material that has a destructive effect on the cell membranes, for example, is methotrexate, that belongs to the group of agents that attacks folic acid, which agents are counted today, along with the alkylating agents, as among the most effective substances for the treatment of neoplasia (abnormal swelling, tumors). A mass of loaded cells suspended in a physiological solution prepared according to the present invention and containing a concentration of methotrexate in the cells and also a material inhibiting attack by the methotrexate on the membranes of the cells, for example, the protein albumin or the sugar sucrose, is therefore an outstandingly successful preparation to inject for the direct treatment of tumors in the liver. Whereas for the treatment of liver tumors with methotrexate, it was heretofore possible merely to inject methotrexate directly into the bloodstream, where it developed its effect throughout the body and thus also attacked healthy tissue, it is now advantageously possible, by use of loaded cell preparations according to the present invention to deliver methotrexate for action directly in the spleen or liver without letting it be distributed over the entire blood circulation system of the body or among a considerable number of organs of the body. In consequence, a smaller dose of methotrexate than was previously necessary for tumor treatment is all that is needed to be introduced into the body, or, likewise, a smaller number of injections than were previously necessary, which has the incidental advantage of reducing or avoiding negative side effects of the introduction of this chemical agent.

A further and likewise very helpful development of the invention is to be found in the incorporation into the loaded cells, from the physiological solution used in the loading material exchange step, of materials in the form of particles having a diameter in the range between 5 and 20 nm. and providing with a coating consisting of liposomes. Since the liposomes, after their release from the loaded cells, are taken up at once by the tissues on the boundaries of the bloodstream, it is thus possible to introduce particular materials into the interior of the tissues of the spleen and liver.

As described above in the introductory description how loaded cell suspensions are prepared, it is necessary in their preparation to raise the permeability in order to enable exchange of material between cells to be loaded and the surrounding physiological solution containing the materials to be loaded into the cells. For carrying out the process of the present invention the permeability increase can be done either by the effect of osmotic pressure or by the effect of an electrical field, according to the requirements of the particular case or according to any other reasons for selection of one or the other procedure.

For the case that the teaching provided in the above-cited German patent and German OS No. 23 26 161 regarding permeability increase by the operation of osmotic pressure is utilized, the process of the present invention can be carried out as follows:

The cells provided for the preparation of the mass of loaded cells are first put into a cell-compatible solution that, for example, can be an aqueous solution containing at least 0.5 mM per liter of magnesium and/or calcium ions as well as potassium ions, the solution having an osmolarity that is so low compared with the osmolarity of the cell content that, as the result of the osmotic pressure thereby produced in the cells, the permeability of the cell membranes is increased—without however destroying the membranes.

Erythrocytes are used for preparation of the loaded cells. The osmolarity difference to be provided amounts approximately to a factor of 15. If the cell-compatible solution does not already contain the materials to be loaded into the cells, this material should then at this point be added. Furthermore, the materials to be included in the cells in accordance with the present invention are also introduced into the cell-compatible solution in the appropriate dosing. After the material exchange between the materials present in the cell-compatible solution and the cell contents through the cell membranes now having an increased permeability, and the content of the thus produced loaded cells practically corresponds to that of the cell-compatible solution, as a next step, the osmolarity of the cell-compatible solution is increased to that of the original cell content by the addition of osmotically active materials, such as calcium, potassium and sodium ions. By osmotically active materials there are here understood materials that have a reflection coefficient of about 0.8, but, however, because they are in general contained in a cell-compatible solution, build up a sufficiently high osmotic pressure. After a dwell time, during which the cell membranes heal up, the loaded cells so formed are separated from the cell-compatible solution and the mass of loaded cells thus produced is poured into an isotonic physiological liquid. When erythrocytes are used, it is practical, for healing away the changes of the cell membranes produced by permeability increase, to let the cells stand for about five minutes at 0° C. and then to warm them up to body temperature for about 30 to 60 minutes.

For the case in which the teaching of German OS No. 24 05 119 regarding permeability increase by the effect of an electric field is to be used, the performance of the method of the present invention is carried out as follows:

The cells provided for the preparation of the mass of loaded cells are put into an electrically conducting liquid forming a cell-compatible electrolyte solution which is preferably at a temperature lying between 0° C. and 25° C. As a next step, the electrolyte solution containing the cells is subjected to an electric field having a strength from $10^3$ to $10^5$ V/cm until the permeability of the cell membranes is increased to such an extent that molecules with a radius of at least 0.5 nm can pass through the cell membranes. For this purpose, it is convenient and practical to pass the electrolyte solution through a focus of an electric field. The resulting permeability increase can be recognized, for example in the application of the process to erythrocytes, by the discoloration of the electrolyte liquid as the result of the hemoglobin going out of the cell interiors and by the decoloration of the erythrocytes. In the case in which the materials and substances that are to be incorporated in the loaded cells are already in the cell-compatible electrolyte solution, the material exchange takes place right after the permeability increase. It is however also possible, after the permeability increase and still before the performance of the healing of the cell membranes, to put the cells into a cell-compatible solution of which the osmolarity corresponds to the osmolarity of the cell content of the original cells. In this cell-compatible solution, in which are contained the materials to be loaded into the cells, the material exchange between these materials and the cell content then takes place. After a dwell time in which the cell membranes heal, the loaded cells thus formed are separated from the cell-compatible solution and the mass of loaded cells thus prepared is then poured into an isotonic physiological solution for preservation and storage. When erythrocytes are used, it is practical to prepare the loaded cells in a potassium chloride solution and then to transfer the loaded cells into an isotonic sodium chloride solution that corresponds to blood serum in its ion concentration and osmolarity.

EXAMPLE I

Erythrocytes that were obtained from citrated blood by two steps of centrifuging were suspended in a solution in a ratio of about 1 part by volume of erythrocytes to 10 parts by volume of solution, in which the solution contained:

105 mM KCl; 20 mM NaCl; 4 mM NgCl$_2$; 7.6 mM Na$_2$HPO$_4$; 2.4 mM NaH$_2$PO$_4$ and 10 mM glucose.

The Na$_2$HPO$_4$ and the NaH$_2$PO$_4$ were added to the solution in order to produce the increase of volume of the loaded cells in accordance with the present invention. The pH value of the solution was 7.2.

In 10 ml of the suspension so produced was exposed in a suitable apparatus for 40 μs at 0° C. to an electric field strength of 12 kV/cm. About 1 minute after application of the electric field, which was followed at once by hemolysis, 5 mM per liter of methotrexate that had been marked with tritium were added to the solution. After the hemolysis, that lasted about 5 minutes, the solution was held at 0° C. for another 5 minutes in order to obtain an equilibrium between the interior of the cells and the external solution that contained the methotrexate. As the next step, the temperature of the solution was raised to 37° C., in order to accelerate the healing up of the changes produced in the cell membranes by the electric field. The healing process was terminated after about 20 minutes. The loaded cells were then centrifuged out for 10 minutes at an acceleration corresponding to 10,000 times the value of the acceleration of gravity and the loaded cell sediment thus obtained was then suspended in a physiological solution of the following composition:

138.6 mM NaCl; 12.3 mM $Na_2HPO_4$ and 2.7 mM $NaH_2PO_4$. The pH value of the solution was 7.4 and the suspension concentration in the solution was 6%.

As a test of a portion of the loaded cells showed, the average volume of the loaded cells so produced, was greater by 35% than that of the original erythrocytes.

200 μl of the physiological solution containing the loaded cells were injected into the tail vein of a mouse. About 10 minutes after the injection it was found that 98% of the injected methotrexate was in the liver of the mouse, after an hour still more than 25% and after another hour still 15%. Even after three hours 10% of the activity of this material could still be detected in the liver.

A loaded cell suspension in a physiological solution as above prepared was stored at 4° C. after about 1 day still 90%, after 2 days 80%, after 4 days still 65% and after 7 days still 53% of the loaded cells were detected in the cell sediment.

In a comparison test involving the preparation of methotrexate loaded cells of the same volume as that of the orginal erythrocytes, 10 ml of the erythrocyte containing suspension first prepared above was exposed, as also described above, to electrical pulses. Immediately after application of the electric pulses, there was added to 25 ml of the suspension a solution of the following composition:

63 mM KCl; 12 mM NaCl; 12.4 mM $MgCl_2$; 4.56 mM $Na_2HPO_4$; 1.44 mM $NaH_2PO_4$, and 6 mM glucose and 5 mM methotrexate that had been marked with tritium. The pH value of the added solution was 7.2 After a further period of 5 minutes at 0° C. there were added 10 ml of a solution of the following composition:

210 mM KCl; 40 mM NaCl; 8 Mm $MgCl_2$; 15.2 mM $Na_2HPO_4$; 4.8 mM $NaH_2PO_4$ and 20 mM glucose and 5 mM methotrexate.

The temperature was then raised to 37° C. The loaded cells thus produced were, after being centrifuged out, suspended in a physiological solution of the above given composition and as in the preceding case, injected into the tail vein of a mouse. 10 minutes after the injection 60% of the injected loaded cells were detected in the liver of the mouse.

In the comparison test, in which the same dose of methotrexate was directly injected into the vein the following values were obtained:

About 10 minutes after the injection about 24% of the methotrexate was accumulated in the liver. After 1 to 2 hours the methotrexate activity in the liver had dropped to less than 1%.

EXAMPLE II

Erythrocytes were suspended in a solution in the volume ratio of 1 to 10 where the solution contained:

105 mM Kcl; 20 mM Nacl; 4 mM $MgCl_2$; 5 mM tris-HCl; 10 mM sucrose, and 10 mM glucose.

In this case, the contrast to Example I, tris-HCl and sucrose were added to the solution in order to produce the volume change of the loaded cells according to the present invention. The pH value of the solution was again 7.2

The loaded cells were, as in Example I, produced by application of an electric field with simultaneous incorporation of methotrexate marked with tritium.

After the centrifuging of the loaded cells out of the solution and the preparation of the solution intended for injection, 500 ml of the physiological solution resulting were injected into the tail vein of a mouse. The same results were thereafter obtained as in Example I.

EXAMPLE III

The loaded cells were formed as described in Example I, except that in addition to the methotrexate marked with tritium, also 0.1% by volume of albumin was added to the solution in which the erythrocytes were exposed to the electric field for increasing their permeability and incorporation of the materials from the solution. The experiments with a mouse produced the same results as in Example I. The loaded cells could be stored in this case at a temperature of about 4° C. for a longer time than in the case of the loaded cells formed according to Example I. After 7 days 75% of the loaded cells could still be detected in the cell sediment.

EXAMPLE IV

Liposome particles were first prepared by use of the method described by C. Huang and J. P. Charlton in Biochem. Biophys. Res. Commun. 1972, 46, 1660. There was added to them 5 mg of lecithin 1 ml of a solution that contained 0.15 M KCl, 0.01 M tris-buffer and 1 mM of methotrexate marked with tritium. The pH value of the added solution was 8. The liposome particles, in which methotrexate was contained, were then formed by the use of ultrasonic waves.

As in Example I, erythrocytes were then exposed to an electric field for increasing the permeability of the membranes of the cells. About 1 minute after the application of the electric field, the solution containing the liposome particles in 1:10 ratio was added to the solution containing the erythrocytes and the loaded cells were then formed.

As in Example I, 200 μl of a physiological solution that contained the loaded cells were injected into the tail vein of a mouse. Ten minutes after the injection practically 100% of the methotrexate dose was detected in the liver, after 1 hour still about 60%.

EXAMPLE IV

Starting with a suspension of erythrocytes of the composition given in Example I, 10 ml of the suspension was exposed to electric pulses in the same way as described in Example I. Immediately after the application of the electric field there were added to the suspension 25 ml of a solution of the following composition:

63 mM KCl; 12 ml NaCl; 2.4 mM $MgCl_2$; 4.56 mM $Na_2HPO_4$; 1.44 mM $NaH_2PO_4$; 6 mM glucose and 5 mM methotrexate that had been marked with tritium. The pH value of the solution was 7.2

After the solution had been allowed to stand further 5 minutes at 0° C., there were added 10 ml of a solution of the following composition:

210 mM KCl; 40 mM NaCl; 8 mM $MgCl_2$; 15.2 mM $Na_2HPO_4$; 4.8 mM $NaH_2PO_4$; 20 mM glucose and 5 mM methotrexate.

The temperature of the solution was then raised to 37° C. for 20 minutes. After being washed twice in isotonic NaCl solution the loaded cells thus formed were incubated for 5 minutes in isotonic phosphate-buffered NaCl solution that contained 5 mm gluta-dialdehyde, the proportion of loaded cells to solution being 1:20 by volume.

After centrifuging out the cells and washing them twice, 300 μl of the cells were incubated in 5,000 μl of physiological solution of the composition given in Example I and 200 μl of this suspension were injected into the tail vein of a mouse. After 10 minutes 95% of the loaded cells were detected in the liver of the mouse.

The loaded cells could be stored at a temperature of about 4° C. for a longer time than the loaded cells according to Example I. After 7 days 85% of the loaded cells could still be detected in the cell sediment.

EXAMPLE VI

For preparation of the loaded cells by the effect of osmotic pressure, erythrocytes were suspended in the volume ratio of 1:1 in isotonic phosphate-buffered NaCl solution of the following composition:

138.6 mM NaCl; 12.3 mM $Na_2HPO_4$ and 2.7 mM $NaH_2PO_4$.
The pH value of the solution was 7.4.

1 ml of the suspension so produced was added, for raising the permeability fo the membranes of the cells, with stirring, to 10 ml of a solution that contained 5 mM of methotrexate that had been marked with tritium, 4 mM of $MgSO_4$ and 50 mM of sucrose. The solution so formed was allowed to stand for 5 minutes at 0° C.

As the next step, the osmolarity of the original solution was again restored, by adding a corresponding amount of a 2-molar KCl solution. The solution was then allowed to stand 5 minutes at 0° C. and then the temperature of the solution was raised for 37° C. and maintained there for 20 minutes, in order to accelerate the healing up of the membranes. After centrifuging the loaded cells so produced out of the solution, the cells were incubated in an isotonic, phosphate-buffered NaCl solution of the above mentioned composition.

The loaded cells so produced contained per unit volume, practically the same quantity of methotrexate as the external medium, mainly 98% of the methotrexate concentration present in the external medium.

When the loading material, if loaded alone in the loaded cells, would lead to premature destruction of the cell membrane, additional material for loading in the interior of the cells is provided in the solution of said loading material, which additional materials form hydrogen bonds or covalent bonds with the loading material that is provided for interaction with substances that may be present outside the loaded cells. The result is that the loading materials are unable to react with the membrane, while their intended effect is nevertheless not impaired. The dosing in the physiological solution provided for material exchange is such that after the incorporation of the main loading material and the additional material in the loaded cells, the interaction of the materials with the cell membrane is hindered for a predetermined time.

For example, if the material methotrexate, that is used for treating tumors, but nevertheless attacks the cell membrane, is incorporated in loaded cells together with a protein, for example albumin, or with a sugar, for example, sucrose or a similar polysaccharide, with the result that the membranes of the loaded cells remain stable about twice as long as would be the case without the addition of protein or sugar.

EXAMPLE VII

Erythrocytes, obtained from citrated blood by new stages of centrifuging are suspended in a solution in the ratio of one part by volume of erythrocytes to ten parts by volume of the solution, the solution containing:

105 mM KCl; 20 mM NaCl; 4 mM $MgCl_2$; 7.6 mM $Na_2HPO_4$; 2.4 mM $NaH_2PO_4$ and 10 mM glucose.
The pH value of the solution was 7.2.

10 ml of the suspension so produced was exposed to an electrical field strength of 12 kV/cm at 0° C. in an apparatus suitable for the purpose for 40 usec. About one minute after the application of the electrical field that was followed with hemolysis, 5 mM per liter of methotrexate that had been marked with tritium and 0.1% by volume of albumin was added to the solution. After the hemolysis, that lasted about five minutes, the solution was held for another five minutes at 0° C. in order that an equilibrium could be reached between the cell interiors and the external solution that contained the methotrexate. As a next step, the temperature of the solution was raised to 37° C., in order to accelerate the healing-up of the changes produced by the electric field in the membranes. The healing-up process was terminated after about twenty minutes. The loaded cells were then centrifuged out for ten minutes under an accelerative force 10,000 times the value of the acceleration of gravity, and the sediment of loaded cells thus obtained was suspended in a physiological solution that had the following composition:

138.6 mM NaCl; 12.3 mM $Na_2HPO_4$; 2.7 mM $NaH_2PO_4$.

The pH value of the solution was 7.4 and the suspension concentration of the solution 6%. In order to determine the effect of the locked-in albumin, after twenty hours, the loaded cells were centrifuged out of the solution and the radioactivity in the solution and in the still intact loaded cells was measured. The same measurements were carried out on loaded cells that were prepared in the same manner as described above, but without inclusion of albumin. A comparison of the measured values showed that after twenty hours 33% more intact cells with locked-in albumin were present than there were without locked-in albumin.

EXAMPLE VIII

For preparation of loaded cells by the effect of osmotic pressure, erythrocytes were suspended in a volume ratio of 1:1 in an isotonic, phosphate-buffered NaCl solution of the following composition:

138.6 mM NaCl; 12.3 mM $Na_2HPO_4$; 2.7 mM $NaH_2PO_4$.
The pH value of the solution was 7.4.

1 ml of the suspension so produced was added, for increasing the permeability of the membranes of the cells, with stirring, to 10 ml of a solution that contained 5 mM of methotrexate that had been marked with tritium, 4 mM of $MgSO_4$ and 50 mM of sucrose. This solution was allowed to stand five minutes at 0° C. As the next step, the osmolarity of the original solution was restored by adding a corresponding quantity of a 2 molar KCl solution. The solution was then allowed to stand another five minutes at 0° C. and immediately thereafter the temperature was raised for twenty minutes to 37° C. in order to accelerate the healing of the membranes. The loaded cells so produced were centrifuged out of the solution, after which the cells were incubated in an isotonic, phosphate-buffered sodium chloride solution of the above-given composition. The loaded cells so produced contained practically the same concentration of methotrexate as the external medium, namely 98%.

A comparative measurement for checking the holding capability of the loaded cells produced showed the same results as in Example VII.

Just as the loaded cells prepared according to previously known methods have been used for releasing medicaments and the like in the bloodstream of animals and of human beings, the present invention is likewise applicable for the release of such materials in particular concentration in the spleen and liver of human beings as well as of other animals, with the particular advantages available only by the practice of the present invention.

The term "animal cells" and "animal body" as used herein except with reference to actual experiments already performed, therefore, are to be understood generally as including human cells and a human body, respectively.

We claim:

1. A process for preparing a mass of loaded cells suspended in a solution which cells by their loading are provided with material intended for chemical or physical interaction with substances present outside the cells, comprising the steps of suspending living animal blood cells selected from the group consisting of erythrocytes, lymphocytes, thrombocytes and leucocytes, and having cell membranes, in a cell-compatible solution, increasing the permeability of the cell membranes by the effect of osmotic pressure or by the effect of an electric field, or both, incorporating loading material selected from the group consisting of medicaments and radionuclides into the cells by passage of said materials from a cell-compatible solution through the membranes of increased permeability, restoring the original permeability of the membranes by healing up the membranes by regeneration effect, then separating the cells from the solution in which they were suspended and putting them for preservation in suspension in a physiological solution, said process incorporating the improvement consisting in that:

in the step of incorporating loading material into the cells from a cell-compatible solution, there is provided in the cell-compatible solution, and therefrom incorporated into the cells, a medicament or a radionuclide intended for and capable of chemical or physical interaction with substances present in the spleen or liver of an animal body and having a destructive effect on the cell membranes by interaction therewith that would lead to premature destruction of the cell membranes in the absence of agents inhibiting such effect, also an osmotically active substance compatible with the cell membranes and having the property of changing the volume of the cells without releasing their contents and thereby causing the loaded cells to differ so greatly from the original cells used in the step of incorporating loading material thereinto, that when the loaded cell suspension in a physiological solution, as prepared by the process, is injected into the bloodstream of an animal body, the loaded cells are treated as foreign bodies and are separated from the blood and broken down by the system of body organs composed of the spleen and liver and their contents are liberated in said organs, and also providing in said cell-compatible solution and therefrom incorporating into the cells and additional material selected from the group consisting of proteins and sugars which is capable of interacting with the material having a destructive effect on the cell membranes, by the formation of hydrogen bridge-bonds or covalent bonds therewith, so as to prevent reaction with the membranes without impairment of the intended effect on substances present in the liver or spleen, said additional material being provided in said cell-compatible solution used in said material incorporating step in such dosing, that after the performance said incorporation step and performance of the step of restoring the original semi-permeability of the loaded cells, the interaction of materials in the loaded cells with the cell membranes will be prevented for a predetermined period of time.

2. A process for preparing a mass of loaded cells suspended in a solution which cells by their loading are provided with material intended for chemical or physical interaction with substances present outside the cells, comprising the steps of suspending living animal cells, selected from the group consisting of erythrocytes, lymphocytes, thrombocytes and leucocytes having cell membranes, in a cell-compatible solution, increasing the permeability of the cell membranes by the effect of osmotic pressure, or by the effect of an electric field, or both, incorporating loading material selected from the group consisting of medicaments and radionuclides into the cells by passage of said material from a cell-compatible solution through the membranes of increased permeability, restoring the original permeability of the membranes by healing up the membranes by regeneration effect, then separating the cells from the solution in which they were suspended and putting them for preservation in suspension in a physiological solution of the same osmolarity as the loaded cell content, said process incorporating the improvement consisting in that:

in the step of incorporating material into the cells, a first material is provided in the cell-compatible solution and is therefrom incorporated into the cells, which material is capable of interaction with substances present in the spleen or liver of an animal body and has a destructive effect on the cell membranes by interaction therewith that would lead to premature destruction of the cell membranes in the absence of agents inhibiting such effect, and there is incorporated into said cells from said solution an additional material selected from the group consisting of proteins and sugars which is capable of interacting with the material having a destructive effect on the cell membranes, by the formation of hydrogen-bridge-bonds or covalent bonds therewith, so as to prevent reaction with the membranes without impairment of the intended effect on substances present in the liver or spleen, and, further, in that the loaded cells formed are subjected to the step of being placed into an isotonic solution in which at least one substance of an organic nature is contained which is capable of producing a change in the cell membranes by a reaction with a lipid or protein layer of the membrane without destruction of the loaded cells, said additional material being provided in said cell-compatible solution used in said material incorporating step in such dosing, that after the performance of said incorporation step and performance of the step of restoring the original semipermeability of the loaded cells, the interaction of materials in the loaded cells with the cell membranes will be prevented for a predetermined period of time and, further, in that the loaded cells are left standing in said isotonic solution for such a time, and the concentration of the substance or substances capable of producing a change in the cell membranes is so selected, that when, after ther preparation of a loaded cell suspension in a physiological solution in accordance with the process said suspension is injected into the bloodstream of an animal body, the loaded cells thereof will be separated from the blood and broken down by the system of body organs composed of the spleen and liver.

* * * * *